United States Patent
Zhang et al.

(10) Patent No.: US 12,245,768 B2
(45) Date of Patent: Mar. 11, 2025

(54) OCCLUDING STENT, IMPLANTER THEREOF, AND IMPLANTING METHOD THEREOF

(71) Applicants: Micro-Tech (Nanjing) Co., Ltd., Nanjing (CN); Jiangsu Province Hospital, Nanjing (CN)

(72) Inventors: Guoxin Zhang, Nanjing (CN); Huaiming Sang, Nanjing (CN); Jianyu Wei, Nanjing (CN); Yun Wang, Nanjing (CN); Lurong Li, Nanjing (CN); Weifeng Zhang, Nanjing (CN); Zhenghua Shen, Nanjing (CN); Changqing Li, Nanjing (CN); Derong Leng, Nanjing (CN)

(73) Assignees: Micro-Tech (Nanjing) Co., Ltd., Nanjing (CN); Jiangsu Province Hospital, Nanjing (CN)

( * ) Notice: Subject to any disclaimer, the term of this patent is extended or adjusted under 35 U.S.C. 154(b) by 128 days.

(21) Appl. No.: 17/059,217

(22) PCT Filed: Mar. 3, 2020

(86) PCT No.: PCT/CN2020/077659
§ 371 (c)(1),
(2) Date: Nov. 26, 2020

(87) PCT Pub. No.: WO2020/177692
PCT Pub. Date: Sep. 10, 2020

(65) Prior Publication Data
US 2021/0196283 A1    Jul. 1, 2021

(30) Foreign Application Priority Data
Mar. 5, 2019  (CN) .......................... 201910164284.0

(51) Int. Cl.
*A61B 17/12* (2006.01)
*A61F 2/82* (2013.01)
*A61F 2/966* (2013.01)

(52) U.S. Cl.
CPC .......... *A61B 17/12104* (2013.01); *A61F 2/82* (2013.01); *A61F 2/966* (2013.01);
(Continued)

(58) Field of Classification Search
CPC ...... A61B 17/12104; A61B 2017/1205; A61B 2017/1215; A61B 2017/12109;
(Continued)

(56) References Cited

U.S. PATENT DOCUMENTS

| 2004/0055606 A1* | 3/2004 | Hendricksen .......... A61F 2/915 128/207.14 |
| 2005/0055082 A1* | 3/2005 | Ben Muvhar ............. A61F 2/90 623/1.15 |

(Continued)

FOREIGN PATENT DOCUMENTS

| CN | 203354626 | 12/2013 |
| CN | 203379145 | 1/2014 |

(Continued)

OTHER PUBLICATIONS

"International Search Report (Form PCT/ISA/210)" of PCT/CN2020/077659, mailed on May 27, 2020, with English translation thereof, pp. 1-8.

(Continued)

*Primary Examiner* — Brigid K Byrd
(74) *Attorney, Agent, or Firm* — Maier & Maier, PLLC

(57) ABSTRACT

Disclosed is an occluding stent. The occluding stent includes a distal flange occluding body, a proximal flange occluding body, and a connection portion. External surfaces of the distal flange occluding body and the proximal flange occlud-
(Continued)

ing body are both provided with a coating. An external surface of the connection portion is wholly or partially provided with a coating. A first occluding coating is provided between the distal flange occluding body and an inner cavity of the connection portion. The present invention overcomes the defect that the existing occluder device for closure of an esophagobronchial fistula is harmful to surrounding tissues, makes the device retractable, enhances the safety of the device, and improves life and treatment of patients. A new safe and effective treatment method for an esophagobronchial fistula is provided.

10 Claims, 15 Drawing Sheets

(52) U.S. Cl.
CPC ............ *A61F 2230/0071* (2013.01); *A61F 2230/0093* (2013.01)

(58) Field of Classification Search
CPC .... A61B 2017/12118; A61B 17/12168; A61B 17/12177; A61B 17/12172; A61B 2017/00575; A61B 2017/00606; A61B 2017/00818; A61F 2/82; A61F 2/966; A61F 2230/0071; A61F 2230/0093; A61F 2/203; A61F 6/146; A61F 6/20
See application file for complete search history.

(56) References Cited

U.S. PATENT DOCUMENTS

| | | | | |
|---|---|---|---|---|
| 2005/0137712 | A1* | 6/2005 | Biggs | A61B 17/12104 600/431 |
| 2006/0135947 | A1* | 6/2006 | Soltesz | A61B 17/12159 604/516 |
| 2014/0343348 | A1* | 11/2014 | Kaplan | A61B 17/12104 604/21 |
| 2014/0371787 | A1 | 12/2014 | Schaeffer | |
| 2019/0099589 | A1* | 4/2019 | Walsh | A61M 27/002 |
| 2019/0298559 | A1* | 10/2019 | Gupta | A61B 17/29 |

FOREIGN PATENT DOCUMENTS

| | | |
|---|---|---|
| CN | 205144808 | 4/2016 |
| CN | 205903284 | 1/2017 |
| CN | 206745406 | 12/2017 |
| CN | 109199469 | 1/2019 |
| CN | 109758204 | 5/2019 |
| CN | 109758205 | 5/2019 |

OTHER PUBLICATIONS

Balazs et al., "Esophagorespiratory fistulas of tumorous origin. Non-operative management of 264 cases in a 20-year period", European Journal of Cardio-thoracic Surgery, 2008, pp. 1103-1107.
Buitrago et al., "Fatal Hemoptysis After Closure of Gastrobronchial Fistula Using an Amplatzer Vascular Device", Ann Thorac Surg, 2018, pp. e71-e73.
Li et al., "Endoscopic closure of refractory upper GI-tracheobronchial fistulas with a novel occluder: a prospective, single-arm, single-center study (with video)", Gastrointestinal Endoscopy, 2023, vol. 97, No. 5, pp. 859-870.
Sang et al., "Tracheoesophageal fistula closed by a new gastrointestinal occluder device", Endoscopy, 2020, 2 pages.
Zhu et al., "Endoscopic closure of tracheoesophageal fistula with a novel dumbbell-shaped occluder", Endoscopy, 2021, 2 pages.

\* cited by examiner

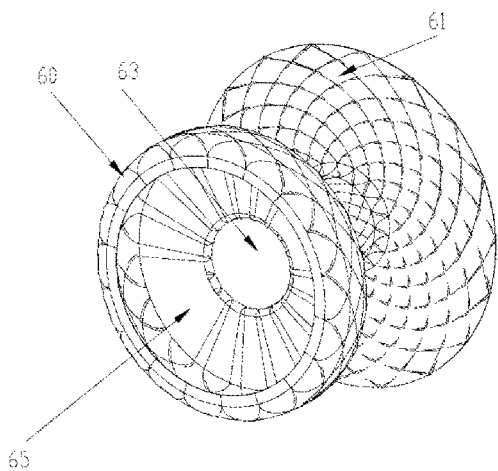 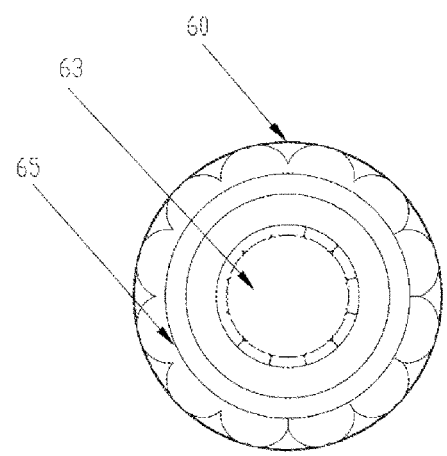
FIG. 25  FIG. 26
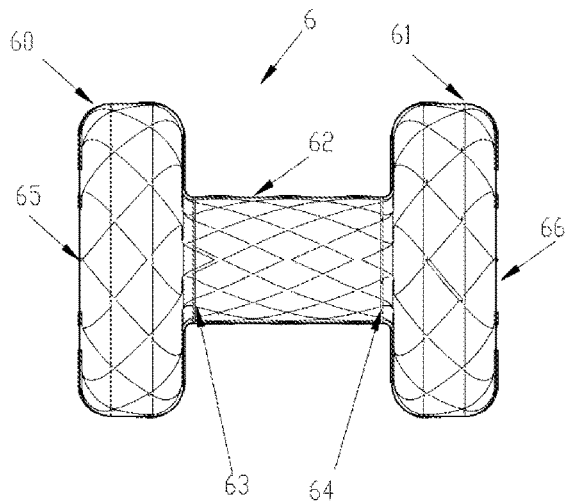
FIG. 27
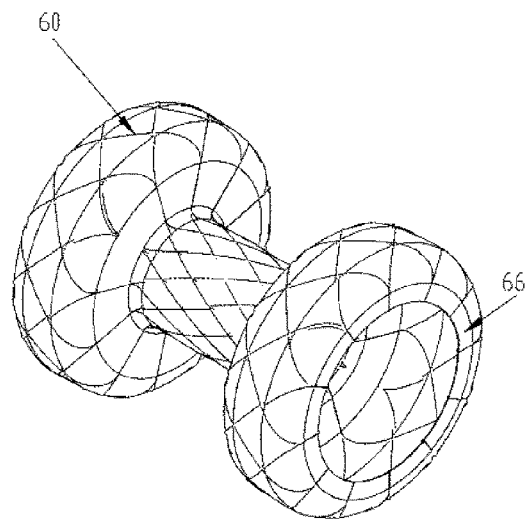
FIG. 28

US 12,245,768 B2

OCCLUDING STENT, IMPLANTER THEREOF, AND IMPLANTING METHOD THEREOF

CROSS-REFERENCE TO RELATED APPLICATION

This application is a 371 of international application of PCT application serial no. PCT/CN2020/077659, filed on Mar. 3, 2020, which claims the priority benefit of China application no. 201910164284.0, filed on Mar. 5, 2019. The entirety of each of the above-mentioned patent applications is hereby incorporated by reference herein and made a part of this specification.

BACKGROUND

Technical Field

The present invention relates to the field of minimally invasive technologies, and in particular, to an occluding stent, an implanter thereof, and an implanting method thereof.

Description of Related Art

In 2006, the first case of an atrial septal occluder used for closure of a 5 mm esophagobronchial fistula was reported in Paulo RS and so on, and the patient left the hospital 5 days after the surgery. Closure from the trachea via a tube causes small invasion, the operation is easy, and the effect is significant. Later, numerous umbrella-shaped devices and other similar mechanical occluding devices are developed based on the atrial septal defect occluder to close esophagobronchial fistulas. However, such devices still have the following disadvantages: (1) The occluder has end covers at proximal and distal ends, or even if the occluder is concave inwards, once the patient coughs, it causes the occluder to be pear-shaped, which easily damages surrounding tissues and causes massive hemorrhage or the like, leading to sudden death. (2) The occluder is liable to corrosion; besides, as a foreign body, the occluder may cause inflammatory reaction, and common occluding devices cannot resist the inflammatory reaction. (3) There is no withdrawal unit; once the occluder is implanted, it cannot be taken out through conservative medical therapy. (4) Generally, the occluder is implanted through the trachea, which affects the rescue channel; in addition, the occluder cannot be implanted under the direct vision of a doctor at any time, which causes certain risks. (5) The treatment method of expanding the esophagus circumferentially by using a conventional stent severely affects the daily life of the patient, causes long-term pain, and affects the life quality of the patient. (6) The occluder itself is heavy; the occluder compresses surrounding tissues, which causes avascular necrosis, or the occluder may even fall off and block the trachea, causing death.

SUMMARY

An object of the present invention is to provide an occluding stent, an implanter thereof, and an implanting method thereof, to solve many defects in the background. The present invention overcomes the defect that the existing occluding device for closure of an esophagobronchial fistula is harmful to surrounding tissues, makes the device retractable, enhances the safety of the device, and improves life and treatment of patients. A new safe and effective treatment method for an esophagobronchial fistula is provided.

To achieve the foregoing objectives, the present invention provides the following technical solutions:

An occluding stent 6 comprises a distal flange occluding body 60, a proximal flange occluding body 61, and a connection portion 62.

Wherein the distal flange occluding body 60 is umbrella-shaped, mushroom cap-shaped, cup-shaped, disc-shaped, bowl-shaped, hemi-spherical or spherical, the proximal flange occluding body 61 is umbrella-shaped, mushroom cap-shaped, cup-shaped or spherical, and a sealed occlusion state is formed between the distal flange occluding body 60 and the proximal flange occluding body 61 by using a coating.

Wherein a surface of the connection portion 62 is wholly or partially provided with a coating; a surface of the distal flange occluding body 60 is wholly or partially provided with a coating; and a surface of the proximal flange occluding body 61 is wholly or partially provided with a coating.

Wherein a first occluding coating 63 is provided between the distal flange occluding body 60 and an inner cavity of the connection portion 62, and/or a second occluding coating 64 is provided between the proximal flange occluding body 61 and the inner cavity of the connection portion 62, to prevent food or foreign objects from entering from one alimentary canal into another alimentary canal, from one airway into one alimentary canal, from one alimentary canal into one airway or from one airway into another airway.

Wherein a surface of the connection portion 62 is provided with a coating in itself, to prevent food or foreign objects from entering from one alimentary canal into another alimentary canal, from one airway into one alimentary canal, from one alimentary canal into one airway or from one airway into another airway.

Wherein a surface of the connection portion 62 is provided with a coating in itself.

Wherein the distal flange occluding body 60 is umbrella-shaped 1, the proximal flange occluding body 61 is mushroom cap-shaped 2, the connection portion 62 is middle stent 3, the umbrella-shaped 1 and the mushroom cap-shaped 2 are connected as a whole through a middle stent 3. The umbrella-shaped stent 1 and the mushroom-shaped stent 2 are connected integrally through the middle stent 3. External surfaces of the umbrella-shaped stent 1, the mushroom-shaped stent 2 and the middle stent 3 are all provided with a coating. The middle stent 3 is of a tubular structure, with both ends being sealed through the coating. The umbrella-shaped stent 1 shapes like an umbrella when being unfolded, and the mushroom-shaped stent 2 shapes like a pileus when being unfolded.

The umbrella-shaped stent 1 includes an umbrella-shaped stent skeleton 101 and an umbrella-shaped stent coating 100. The umbrella-shaped stent skeleton 101 is of a dispersed structure or a braided structure. The umbrella-shaped stent coating 100 covers the surface of the umbrella-shaped stent skeleton 101.

The mushroom-shaped stent 2 includes a mushroom-shaped stent radial skeleton 21 and a mushroom-shaped stent coating 20. The mushroom-shaped stent coating 20 is provided on the surface of the mushroom-shaped stent radial skeleton 21. The mushroom-shaped stent radial skeleton 21 includes a mushroom-shaped stent longitudinal skeleton 23, a mushroom-shaped stent proximal skeleton 24, and a mushroom-shaped stent distal skeleton 25.

The middle stent 3 includes a middle stent skeleton 31 and a middle stent coating 30. Two ends of the middle stent skeleton 31 are integrally connected with the umbrella-shaped stent 1 and the mushroom-shaped stent 2 respectively. A middle stent coating 30 is provided on the surface of the middle stent skeleton 31.

An esophagus-end occluding coating 4 is provided at one end of the middle stent 3, and a trachea-end occluding coating 5 is provided at the other end of the middle stent 3.

The umbrella-shaped stent 1 is formed by a metal wire structure. The metal wire is made of any one or more of the following materials: a biologically compatible nickel-titanium alloy, a bioresorbable polymer, a shape-memory polymer, a resorbable metal, and a biologically compatible metal.

The mushroom-shaped stent 2 is formed by a metal wire structure. The metal wire is made of any one or more of the following materials: a biologically compatible nickel-titanium alloy, a bioresorbable polymer, a shape-memory polymer, a resorbable metal, and a biologically compatible metal.

The middle stent 3 is formed by a metal wire structure. The metal wire is made of any one or more of the following materials: a biologically compatible nickel-titanium alloy, a bioresorbable polymer, a shape-memory polymer, a resorbable metal, and a biologically compatible metal. A corrosion-resistant coating is provided on an external surface of the metal wire, and the corrosion-resistant coating is made of silicone. An antibacterial coating is made of an organosilicon cation-containing steroid, minocycline, rifampicin, gentamicin, vancomycin, or a hydrophobic material, or a combination thereof.

An occluding stent delivery, characterized in that an occluding stent 6 is loaded at a distal end of an outer tube, a proximal end of the outer tube is connected to a front handle 115, a middle tube is located in the outer tube, and the middle tube is connected to a rear handle; the front handle 115 is retracted, the outer tube retreats, and the middle tube ejects and releases a distal flange of the occluding stent 6; the implanter is retracted into a proximal tissue, and then a proximal flange of the occluding stent 6 is deployed.

An occluding stent implanter, characterized by comprising a rear handle 8, a rear pushrod 9, and a front handle 115, wherein the rear pushrod 9 is fixedly connected to the rear handle 8, the rear pushrod 9 passes through the interior of the front handle 115, a distal end of the rear pushrod 9 is connected to a front pushrod 92 through an inner connection hose 91, a mushroom-shaped front pusher 93 is connected at a distal end of the front pushrod 92, a flexible tube 94 is sleeved outside the front pushrod 92, a proximal end of the front handle 115 is connected to a rear pushrod locking knob 110 through threads, a distal end of the rear pushrod locking knob 110 is provided with a tapered rubber plug 113, and the tapered rubber plug 113 is in contact with a tapered inner wall 111 inside the front handle 115.

Wherein a proximal end of the rear handle 8 is provided with a rear-handle rear cover, a rear-handle front cover 81 is connected at a distal end of the rear handle 8, and the rear pushrod 9 is fixedly connected to the rear handle 8 through a rear pushrod holder 90;

The front handle 115 is provided with a Luer taper tube 112 in communication with an inner cavity 114 of the front handle 115, a distal end of the front handle 115 is connected to a front-handle front cover 117 through a connecting sleeve 116, and a distal end of the front-handle front cover 117 is provided with a flexible sleeve hose connecting tube 118; a flexible tube 94 is connected on the sleeve hose connecting tube 118; the tapered rubber plug 113 is provided with a through hole 1131 for the rear pushrod 9 to pass through, the tapered rubber plug 113 has a tapered surface 1132 in contact with the tapered inner wall 111, and the tapered rubber plug 113 is provided with a cross recess 1133.

The plugging stent insertion device is also provided with an inner hole for the guide wire to pass through one side of the occluding stent.

Wherein a range-adjustable mark is provided on the rear pushrod 9 between the rear pushrod locking knob 110 and the rear-handle front cover 81 of the implanter, the range-adjustable mark comprises a positioning nut 805 located at a distal end and a range adjuster 806 that is located at a proximal end and connected to the positioning nut 805 through threads, the positioning nut 805 is provided with an anti-slip rib 808, the range adjuster 806 is provided with an alary protrusion 807, the positioning nut 805 and the range adjuster 806 are sleeved over the rear pushrod 9, and the range adjuster 806 is screwed in or out to adjust a distance between the rear pushrod locking knob 110 and the rear-handle front cover 81.

Wherein a removable mark is provided on the rear pushrod 9 between the rear pushrod locking knob 110 and the rear-handle front cover 81 of the implanter, the removable mark is sleeved over the rear pushrod 9 and comprises a removable sleeve 801 and an anti-slip handle 802, the removable sleeve 801 and the anti-slip handle 802 are connected through a connector 804, a notch 803 for allowing the rear pushrod 9 to enter is provided on a side of the removable sleeve 801, the removable mark is sleeved over the rear pushrod 9 through the notch 803, and connection is implemented replying on an elastic force of the removable sleeve 801, so that a distance between the rear pushrod locking knob 110 and the rear-handle front cover 81 is locked.

Compared with the prior art, the present invention has the following beneficial effects:

In the present invention, because the distal end and the proximal end of the occluding stent are single-layer structures, the occluding stent is lighter than a disc-shaped structure of a vascular occluder, and surrounding tissues of the fistula have a lower necrosis risk. In addition, the esophagus end is larger than the trachea end, and the risk of the occluder falling into the trachea is further reduced. The stent has no end cover. Even if the occluder is deformed to be pear-shaped, it does not touch the surrounding tissues. Moreover, the occluding stent is released under the direct vision of the gastroscope, so that operations of the doctor are more reliable. The stent is provided with a withdraw line at the proximal end, and can be taken out at any time through conservative medical therapy. Even if falling into the trachea, the stent can be taken out by using foreign body forceps. The present invention substitutes the treatment method of expanding the esophagus circumferentially by using a conventional stent, the esophagus is not compressed, thereby alleviating the pain and improving the life quality of the patient. The stent is lighter than an occluder and has smaller compression on surrounding tissues, so that the surrounding tissues have a lower risk of avascular necrosis.

BRIEF DESCRIPTION OF THE DRAWINGS

FIG. 25 is a second three-dimensional schematic diagram of the occluding stent in Embodiment 9 of the present invention.

FIG. 26 is a side schematic structural diagram of an occluding stent in Embodiment 10 of the present invention.

FIG. 27 is an overall schematic structural diagram of the occluding stent in Embodiment 10 of the present invention.

FIG. 28 is a three-dimensional schematic diagram of the occluding stent in Embodiment 10 of the present invention.

Figure 1:
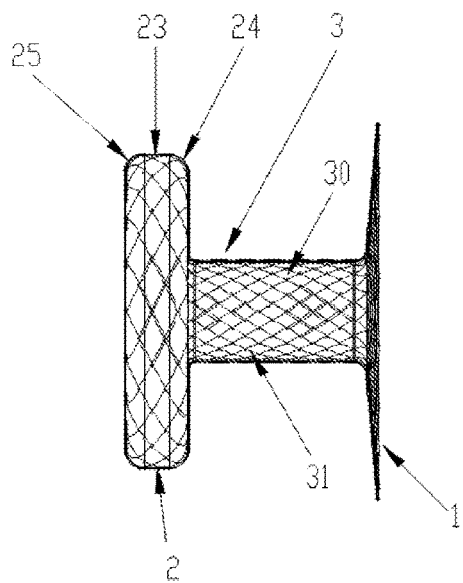
FIG. 1 is a schematic structural diagram of Embodiment 1 of a stent according to the present invention.
Figure 2:
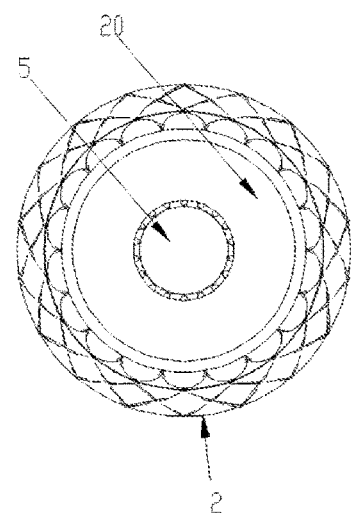
FIG. 2 is a side view of Embodiment 1 of a stent according to the present invention.
Figure 3:
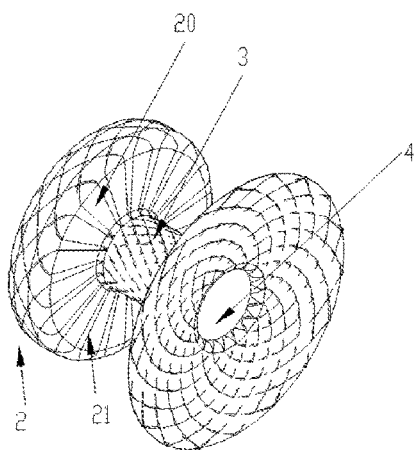
FIG. 3 is a three-dimensional schematic structural diagram of Embodiment 1 of a stent according to the present invention.
Figure 4:
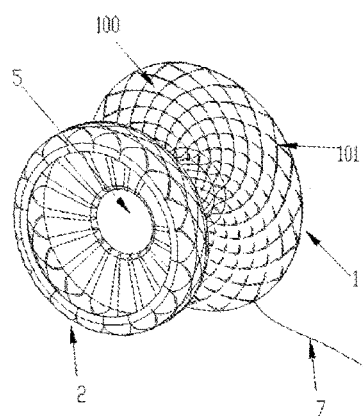
FIG. 4 is a three-dimensional schematic structural diagram of Embodiment 1 of a stent according to the present invention.

In the drawings: 1, umbrella-shaped stent; 100, umbrella-shaped stent coating; 101, umbrella-shaped stent skeleton; 2, mushroom-shaped stent; 20, mushroom-shaped stent coating; 21, mushroom-shaped stent radial skeleton; 23, mushroom-shaped stent longitudinal skeleton; 24, mushroom-shaped stent proximal skeleton; 25, mushroom-shaped stent distal skeleton; 3, middle stent; 30, middle stent coating; 31, middle stent skeleton; 4, esophagus-end occluding coating; 5, trachea-end occluding coating; 7, withdraw line; 8, rear handle; 80, rear-handle rear cover; 81, rear-handle front cover; 9, rear pushrod; 90, rear pushrod holder; 91, inner connection hose; 92, front pushrod; 93, front pusher; 94, flexible tube; 95, precise locating sleeve; 110, rear pushrod locking knob; 111, tapered inner wall; 112, Luer taper tube;

113, tapered rubber plug; 114, inner cavity; 115, front handle; 116, connecting sleeve; 117, front-handle front cover; 118, sleeve hose connecting tube; 1131, through hole; 1132, tapered surface; 1133, cross recess; 1A, mirror umbrella-shaped stent; 119, first target; 120, second target; 6, occluding stent; 60, distal flange occluding body; 61, proximal flange occluding body; 62, connection portion; 63, first occluding coating; 64, second occluding coating; 65, first occluding portion end; 66, second occluding end; 801, removable sleeve; 802, anti-slip handle; 803, notch; 804, connector; 805, positioning nut; 806, range adjuster; 807, alary protrusion; 808, anti-slip rib.

DESCRIPTION OF THE EMBODIMENTS

The technical solutions in the embodiments of the present invention are described clearly and completely below with reference to the accompanying drawings in the embodiments of the present invention. Apparently, the described embodiments are merely some embodiments, rather than all embodiments, of the present invention. All other embodiments obtained by a person of ordinary skill in the art based on the embodiments in the present invention without creative efforts belong to the protection scope of the present invention.

In the description of the present invention, it should be appreciated that the directions or positional relations indicated by the terms such as "center", "longitudinal", "lateral", "length", "width", "thickness", "upper", "lower", "front", "rear", "left", "right", "vertical", "horizontal", "top", "bottom", "inner", "outer", "clockwise" and "anticlockwise" are directions or positional relations based on the drawings, and are merely used for describing the present invention and simplifying the description, rather than indicating or implying that a described device or element needs to have a specific direction or be constructed and operated in a specific direction. Therefore, such terms cannot be construed as a limitation on the present invention.

In FIG. 1 to FIG. 51, the term "proximal end" represents an end close to an operator, and the term "distal end" represents an end away from the operator.

Embodiment 1

As shown in FIG. 1 to FIG. 4, characterized in that, an occluding stent includes an umbrella-shaped stent 1, a mushroom-shaped stent 2, and a middle stent 3. The umbrella-shaped stent 1 and the mushroom-shaped stent 2 are connected integrally through the middle stent 3. External surfaces of the umbrella-shaped stent 1, the mushroom-shaped stent 2 and the middle stent 3 are all provided with a coating. The middle stent 3 is of a tubular structure, with both ends being sealed through the coating. The umbrella-shaped stent 1 shapes like an umbrella when being unfolded, and the mushroom-shaped stent 2 shapes like a pileus when being unfolded.

The umbrella-shaped stent 1 includes an umbrella-shaped stent skeleton 101 and an umbrella-shaped stent coating 100. The umbrella-shaped stent skeleton 101 is of a dispersed structure or a braided structure. The umbrella-shaped stent coating 100 covers the surface of the umbrella-shaped stent skeleton 101.

The mushroom-shaped stent 2 includes a mushroom-shaped stent radial skeleton 21 and a mushroom-shaped stent coating 20. The mushroom-shaped stent coating 20 is provided on the surface of the mushroom-shaped stent radial skeleton 21. The mushroom-shaped stent radial skeleton 21 includes a mushroom-shaped stent longitudinal skeleton 23, a mushroom-shaped stent proximal skeleton 24, and a mushroom-shaped stent distal skeleton 25.

The middle stent 3 includes a middle stent skeleton 31 and a middle stent coating 30. Two ends of the middle stent skeleton 31 are integrally connected with the umbrella-shaped stent 1 and the mushroom-shaped stent 2 respectively. A middle stent coating 30 is provided on the surface of the middle stent skeleton 31.

An esophagus-end occluding coating 4 is provided at one end of the middle stent 3, and a trachea-end occluding coating 5 is provided at the other end of the middle stent 3.

The umbrella-shaped stent 1 is formed by a metal wire structure. The metal wire is made of any one or more of the following materials: a biologically compatible nickel-titanium alloy, a bioresorbable polymer, a shape-memory polymer, a resorbable metal, and a biologically compatible metal.

The mushroom-shaped stent 2 is formed by a metal wire structure. The metal wire is made of any one or more of the following materials: a biologically compatible nickel-titanium alloy, a bioresorbable polymer, a shape-memory polymer, a resorbable metal, and a biologically compatible metal.

The middle stent 3 is formed by a metal wire structure. The metal wire is made of any one or more of the following materials: a biologically compatible nickel-titanium alloy, a bioresorbable polymer, a shape-memory polymer, a resorbable metal, and a biologically compatible metal.

A corrosion-resistant coating is provided on an external surface of the metal wire, and the corrosion-resistant coating is made of silicone. An antibacterial coating is made of an organosilicon cation-containing steroid, minocycline, rifampicin, gentamicin, vancomycin, or a hydrophobic material, or a combination thereof.

A withdraw line 7 is connected on the umbrella-shaped stent 1. The withdraw line 7 may be a metal wire made of the material mentioned above, or a non-metal material with good biological compatibility.

Embodiment 2

Figure 5:
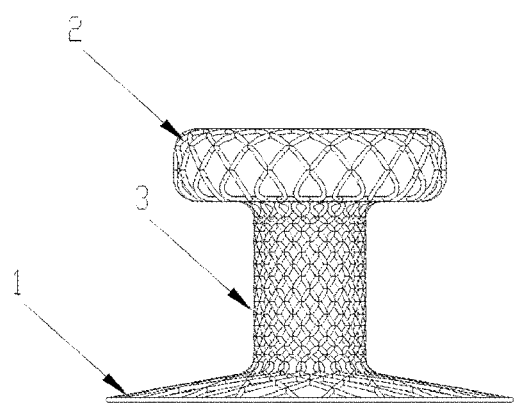
FIG. 5 is a schematic structural diagram of Embodiment 2 of a stent according to the present invention.
Figure 6:
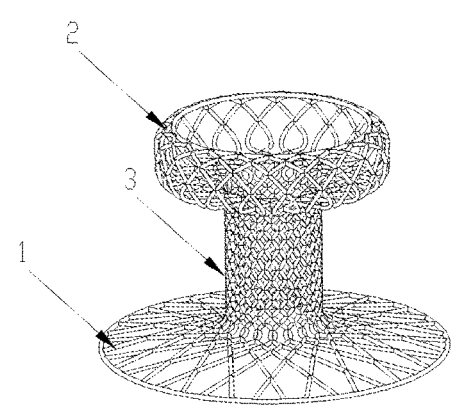
FIG. 6 is a three-dimensional schematic structural diagram of Embodiment 2 of a stent according to the present invention.

As shown in FIG. 5 and FIG. 6, an occluding stent is provided, where the metal wire adopts a braided structure and form that are different from those in Embodiment 1, characterized in that, the occluding stent includes an umbrella-shaped stent 1, a mushroom-shaped stent 2, and a middle stent 3. The umbrella-shaped stent 1 and the mushroom-shaped stent 2 are connected integrally through the middle stent 3. External surfaces of the umbrella-shaped stent 1, the mushroom-shaped stent 2 and the middle stent 3 are all provided with a coating. The middle stent 3 is of a tubular structure, with both ends being sealed through the coating. The umbrella-shaped stent 1 shapes like an umbrella when being unfolded, and the mushroom-shaped stent 2 shapes like a pileus when being unfolded.

Embodiment 3

Figure 7:
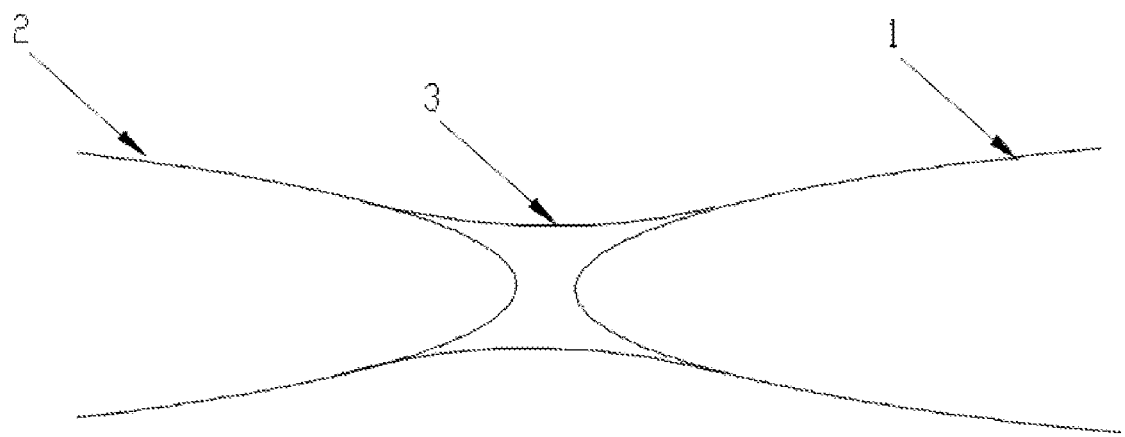
FIG. 7 is a cross-sectional schematic structural diagram of a stent located in an implanter according to the present invention.

FIG. 7 is a cross-sectional schematic structural diagram of a stent located in an implanter according to the present invention. The whole stent is compressed and folded in the tubular structure of the implanter, and is delivered to a target esophagobronchial fistula area.

Figure 8:
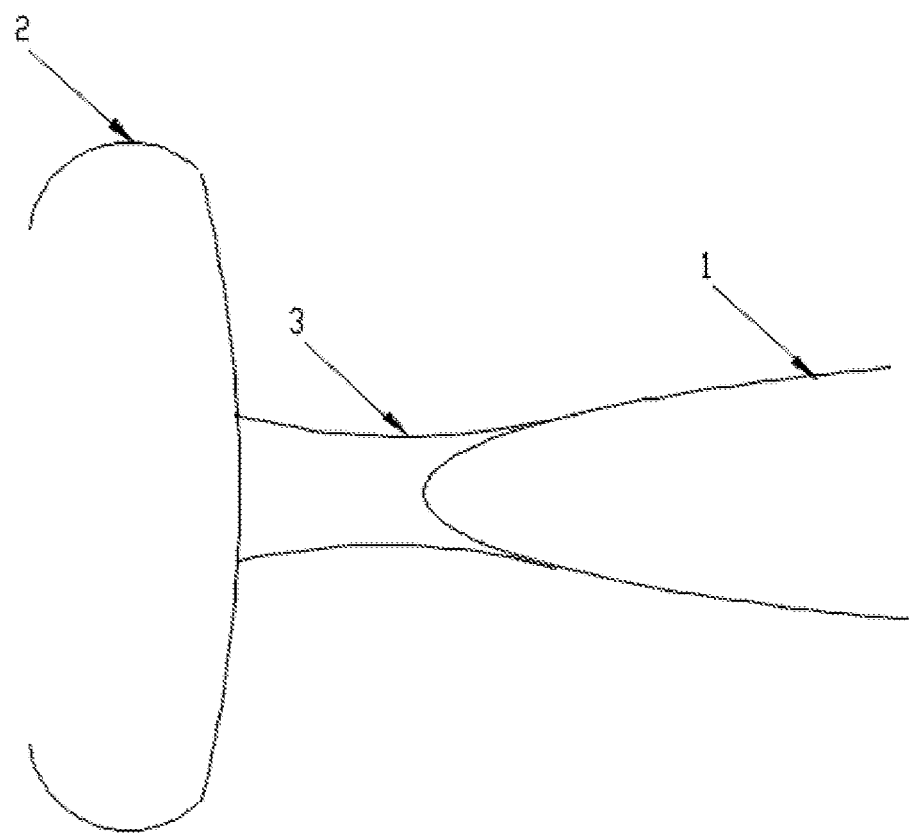
FIG. 8 is a cross-sectional schematic structural diagram of a partial unfolded state of a stent partially located in an implanter according to the present invention.

FIG. 8 is a cross-sectional schematic structural diagram of a partial unfolded state of a stent partially located in an implanter according to the present invention. An end of the stent which is located at the esophagus side or the trachea side is pushed out by the implanter, and is unfolded under the effect of its own elastic force and a memory tension. Then, during a retraction process of the implanter, the other end of the stent is pushed out, released and unfolded, to complete closure of the esophagobronchial fistula.

Embodiment 4

Figure 9A:
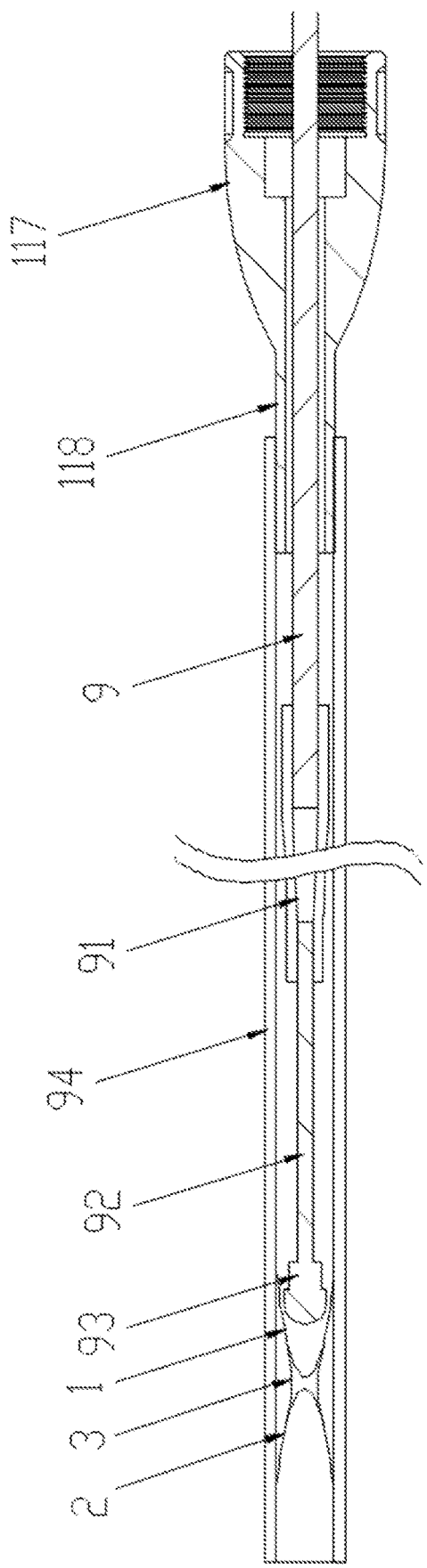
FIG. 9a is a first sectional schematic structural diagram of an implanter according to the present invention.
Figure 9B:
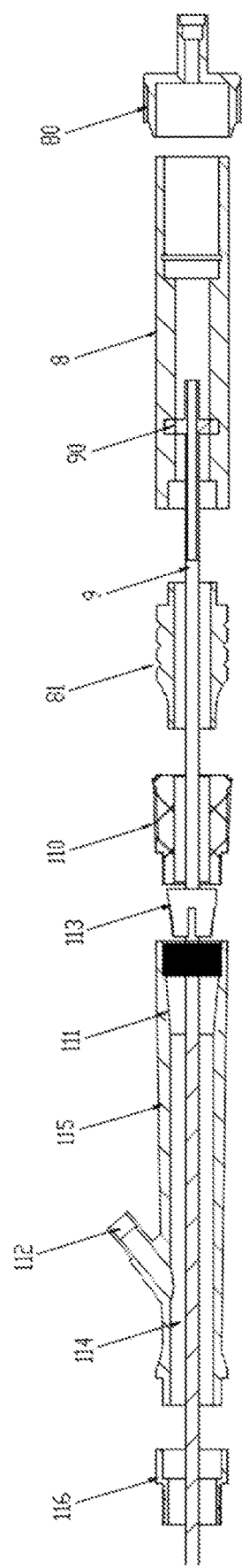
FIG. 9b is a second sectional schematic structural diagram of the implanter according to the present invention.
Figure 10:
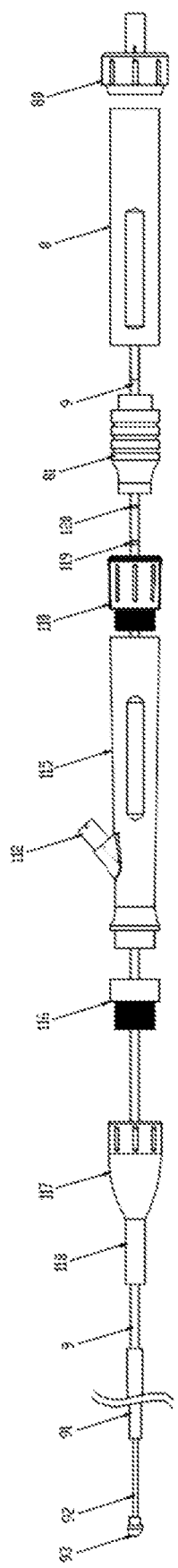
FIG. 10 is an exploded schematic structural diagram of the implanter according to the present invention.
Figure 11:
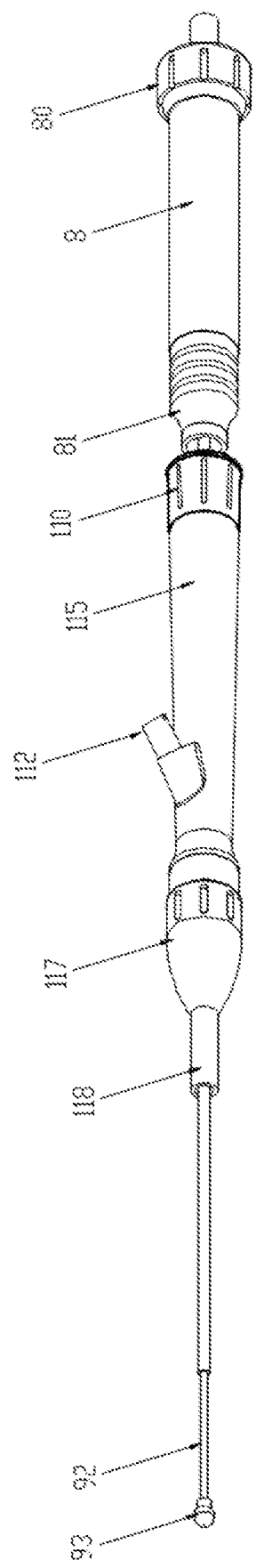
FIG. 11 is a schematic structural diagram of overall assembly of the implanter according to the present invention.
Figure 12:
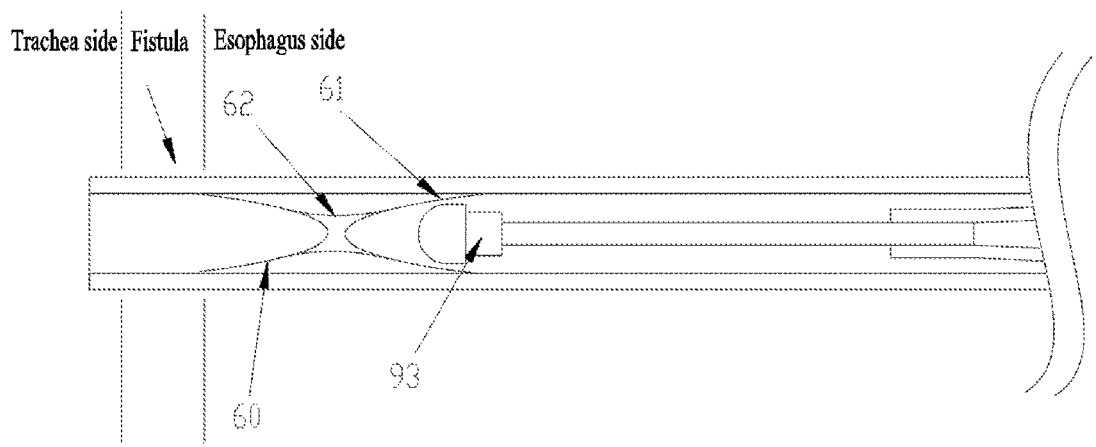
FIG. 12 is a schematic diagram of a first breakdown step of implanting a stent into an esophagobronchial fistula by using an implanter according to the present invention.
Figure 13:
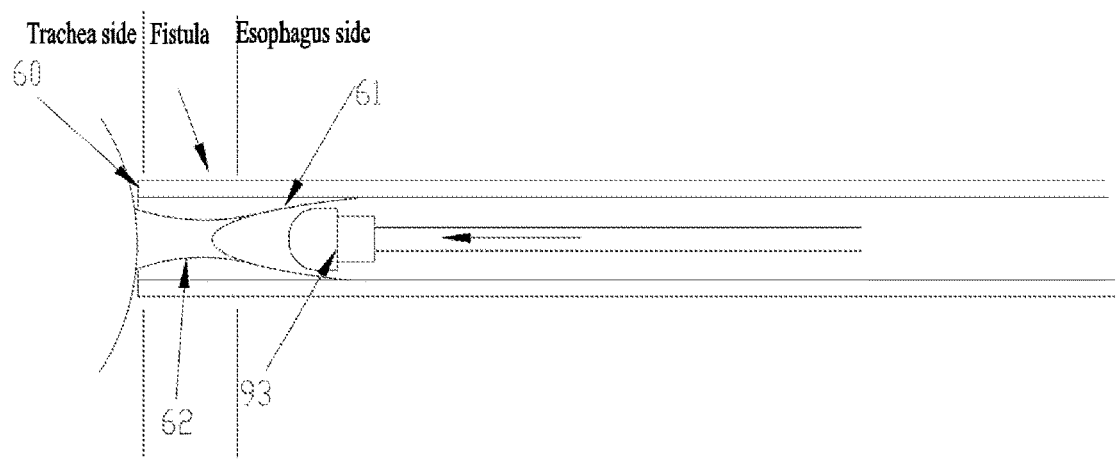
FIG. 13 is a schematic diagram of a second breakdown step of implanting the stent into the esophagobronchial fistula by using the implanter according to the present invention.
Figure 14:
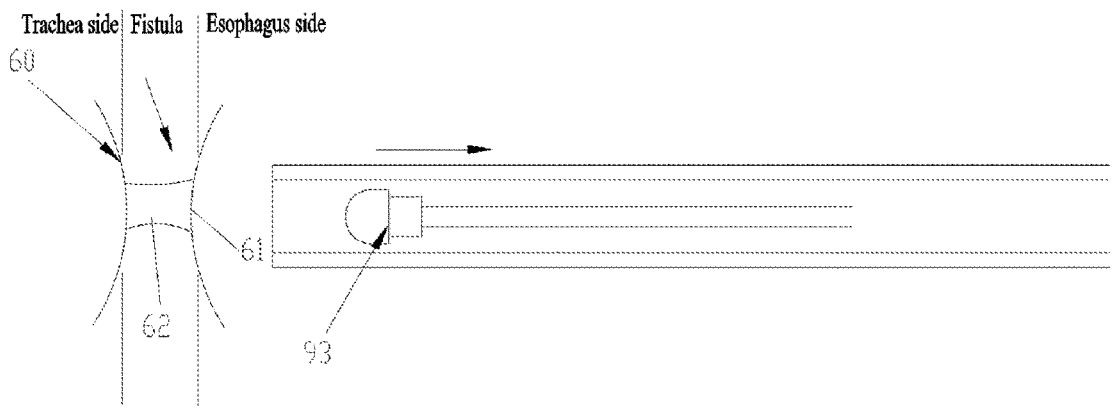
FIG. 14 is a schematic diagram of a third breakdown step of implanting the stent into the esophagobronchial fistula by using the implanter according to the present invention.
Figure 15:
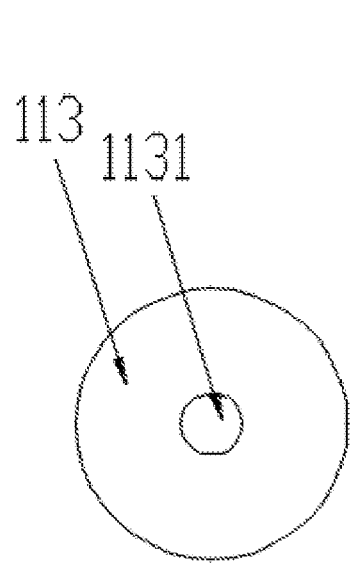
FIG. 15 is a first schematic structural diagram of a tapered rubber plug according to the present invention.
Figure 16:
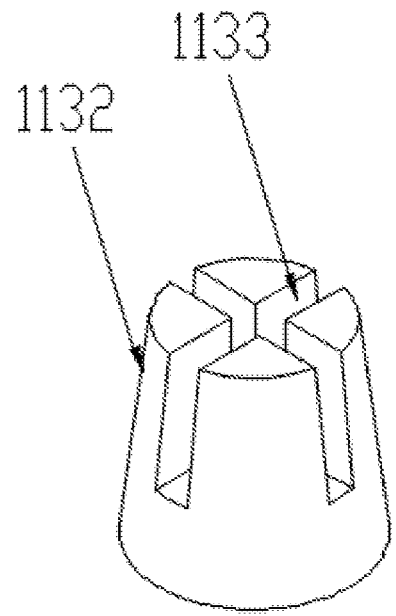
FIG. 16 is a second schematic structural diagram of the tapered rubber plug according to the present invention.
Figure 17:
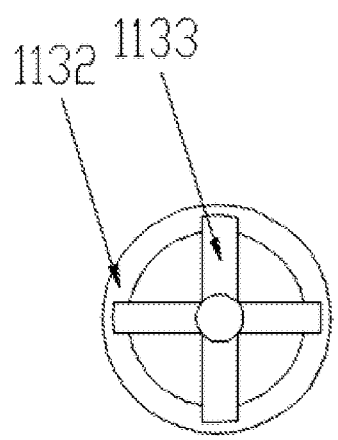
FIG. 17 is a third schematic structural diagram of the tapered rubber plug according to the present invention.
Figure 18:
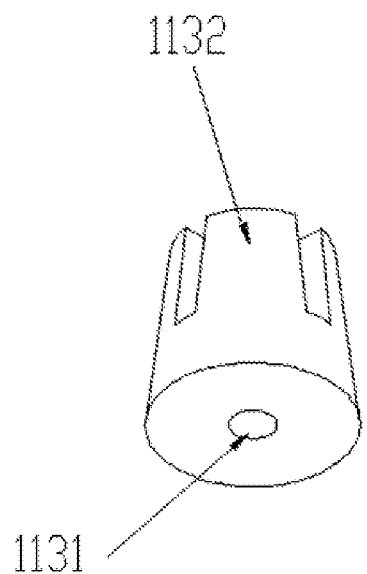
FIG. 18 is a fourth schematic structural diagram of the tapered rubber plug according to the present invention.
Figure 19:
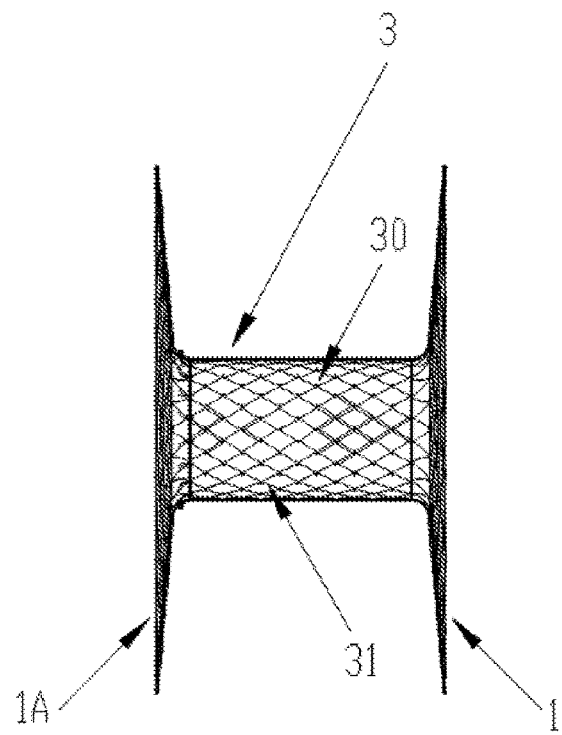
FIG. 19 is a schematic structural diagram of another occluding stent according to the present invention.

FIG. 9a is a first sectional schematic structural diagram of an implanter according to the present invention. FIG. 9b is a second sectional schematic structural diagram of the implanter according to the present invention. FIG. 10 is an exploded schematic structural diagram of the implanter according to the present invention. FIG. 11 is a schematic structural diagram of overall assembly of the implanter according to the present invention.

An occluding stent implanter includes a rear handle 8, a rear pushrod 9 and a front handle 115. The rear pushrod 9 is fixedly connected to the rear handle 8. The rear pushrod 9 passes through the interior of the front handle 115. A distal end of the rear pushrod 9 is connected to a front pushrod 92 through an inner connection hose 91. A mushroom-shaped front pusher 93 is connected at the distal end of the front pushrod 92. A flexible tube 94 is sleeved over the front pushrod 92. A proximal end of the front handle 115 is connected to a rear pushrod locking knob 110 through threads. A tapered rubber plug 113 is disposed at a distal end of the rear pushrod locking knob 110. The tapered rubber plug 113 is in contact with a tapered inner wall 111 inside the front handle 115.

The rear pushrod 9 is a metal rod. The front pusher 93, the rear handle 8 and the front handle 115 may be made of plastic through molding. The inner connection hose 91 and the flexible tube 94 are hoses made of a flexible material.

A rear-handle rear cover 80 is provided at a proximal end of the rear handle 8. A rear-handle front cover 81 is connected at a distal end of the rear handle 8. The rear pushrod 9 is fixedly connected to the rear handle 8 through a rear pushrod holder 90.

The front handle 115 is provided with a Luer taper tube 112 in communication with an inner cavity 114 of the front handle 115. A distal end of the front handle 115 is connected to a front-handle front cover 117 through a connecting sleeve 116, and a flexible sleeve hose connecting tube 118 is disposed at a distal end of the front-handle front cover 117. A flexible tube 94 is connected on the sleeve hose connecting tube 118. The tapered rubber plug 113 is made of a rubber and is elastic. The tapered rubber plug 113 is provided with a through hole 1131 for the rear pushrod 9 to pass through. The tapered rubber plug 113 has a tapered surface 1132 in contact with the tapered inner wall 111, and the tapered rubber plug 113 is provided with a cross recess 1133.

The Luer taper tube 112 may be connected to a syringe or the like, to wash or suction the inner cavity 114.

Embodiment 5

The mushroom-shaped stent 2 may be replaced with a mirror umbrella-shaped stent 1A of which two ends are symmetrical about a mirror line.

Embodiment 6

Figure 20:
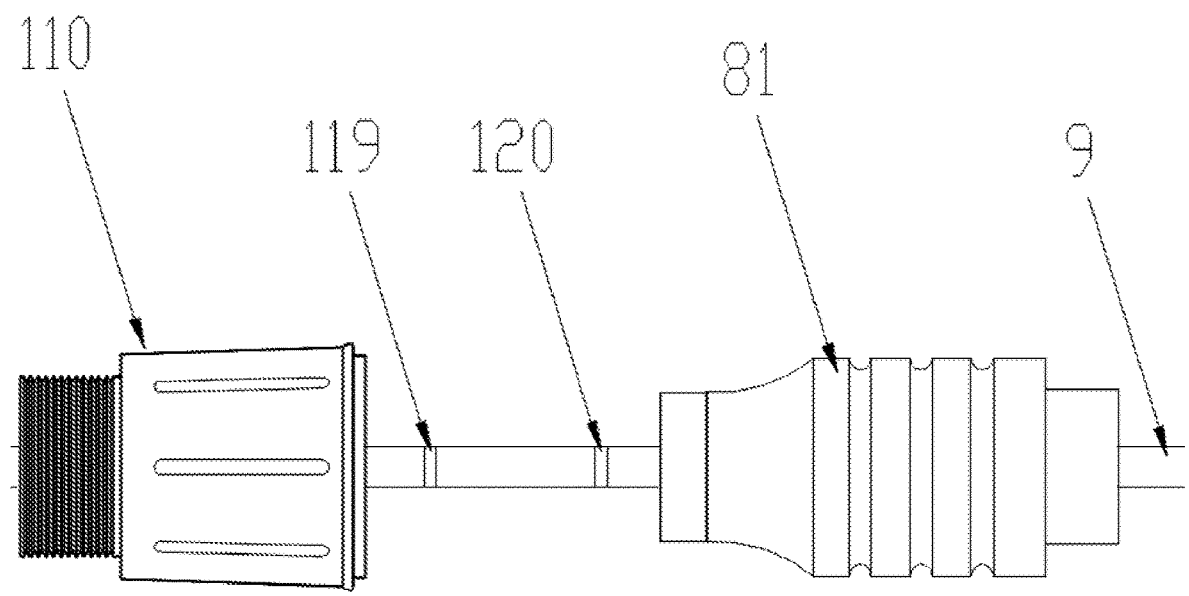
FIG. 20 is a schematic structural diagram of a first target and a second target according to the present invention.

FIG. 20 is a schematic structural diagram of a first target and a second target according to the present invention. The rear pushrod 9 is further provided with a first target 119 and a second target 120. The first target 119 and the second target 120 are a yellow scale mark and a red scale mark respectively, which represent that releasing of the trachea-side stent is started and releasing of the trachea-side stent is completed respectively.

Embodiment 7

Figures 21, 22:
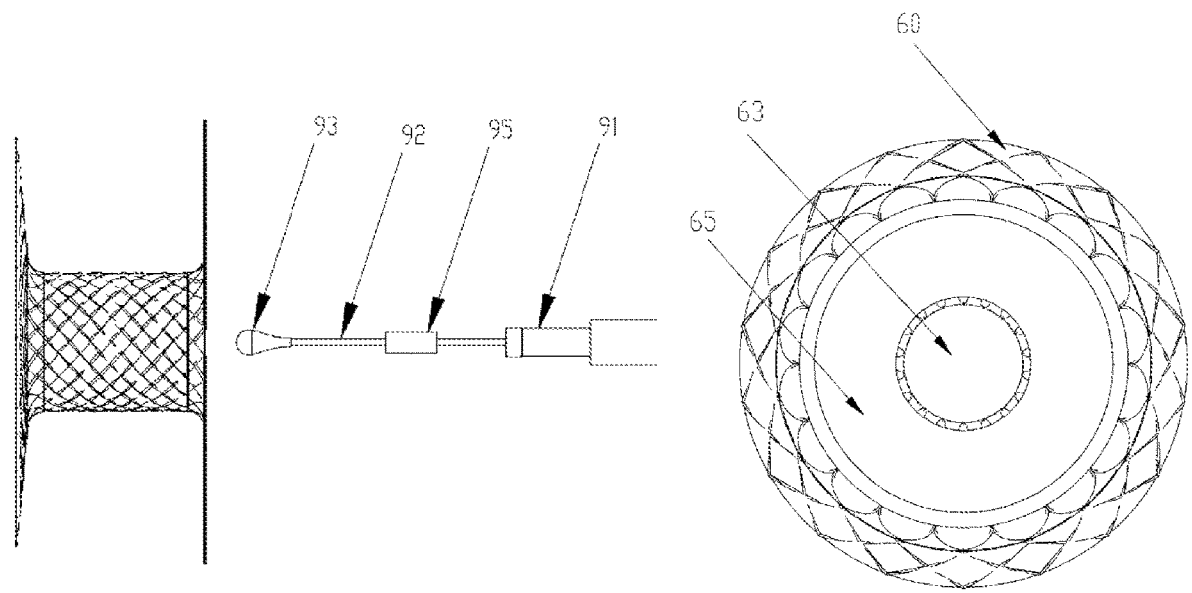
FIG. 21 is a schematic structural diagram of Embodiment 8 of the present invention.
FIG. 22 is a side schematic structural diagram of an occluding stent in Embodiment 9 of the present invention.
Figures 23, 24:
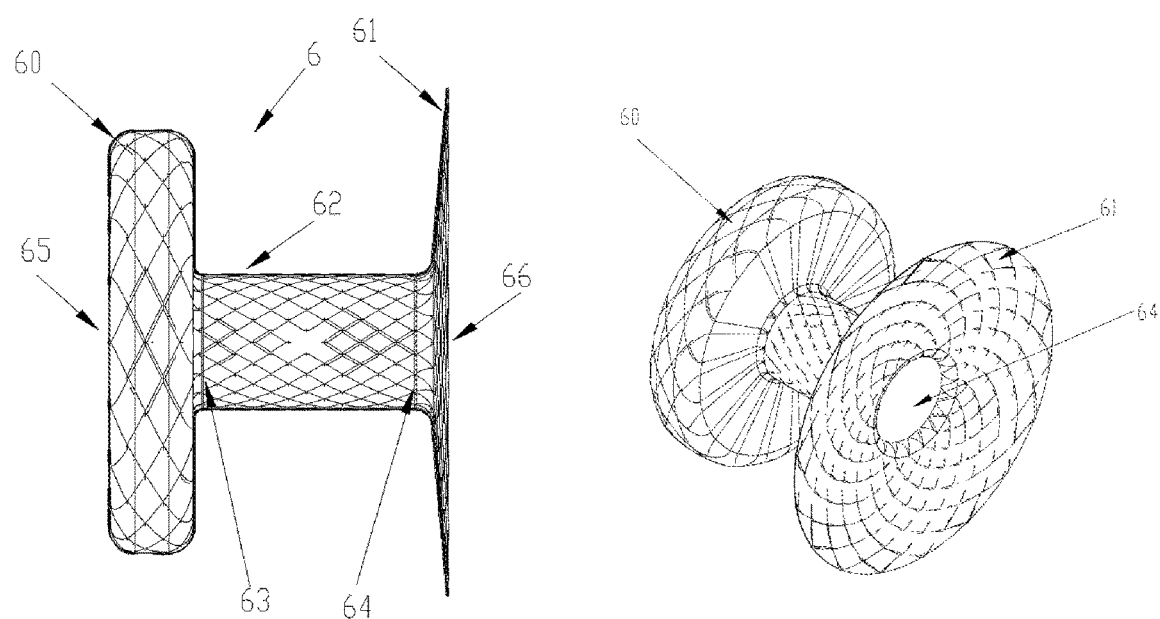
FIG. 23 is an overall schematic structural diagram of the occluding stent in Embodiment 9 of the present invention.
FIG. 24 is a first three-dimensional schematic diagram of the occluding stent in Embodiment 9 of the present invention.
Figure 29:
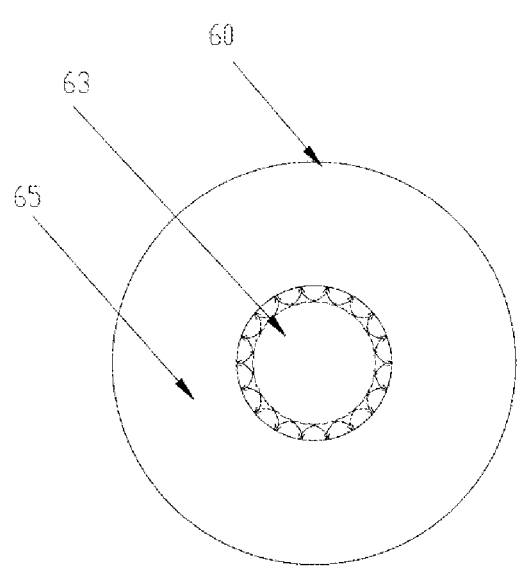
FIG. 29 is a side schematic structural diagram of an occluding stent in Embodiment 11 of the present invention.
Figure 30:
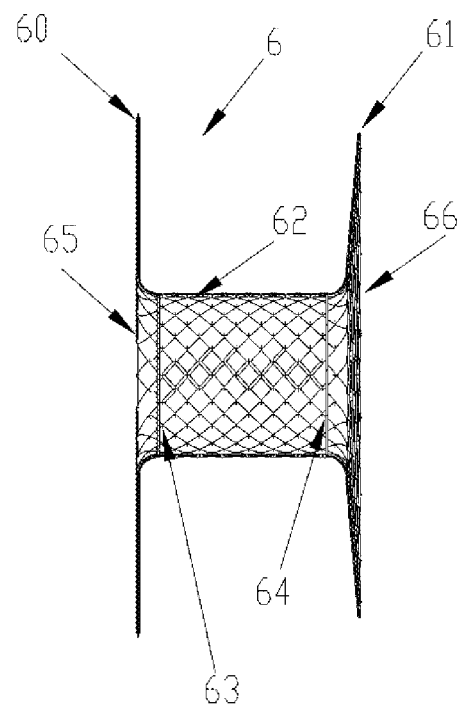
FIG. 30 is an overall schematic structural diagram of the occluding stent in Embodiment 11 of the present invention.
Figure 31:
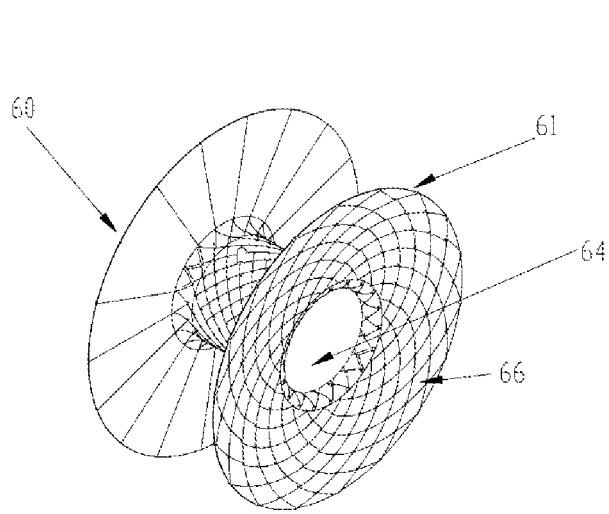
FIG. 31 is a first three-dimensional schematic diagram of the occluding stent in Embodiment 11 of the present invention.
Figure 32:
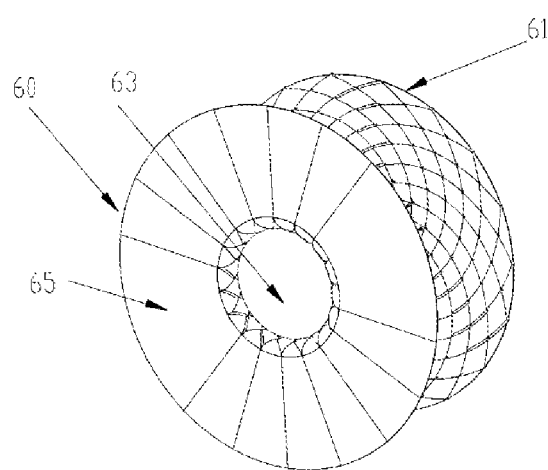
FIG. 32 is a second three-dimensional schematic diagram of the occluding stent in Embodiment 11 of the present invention.
Figure 33:
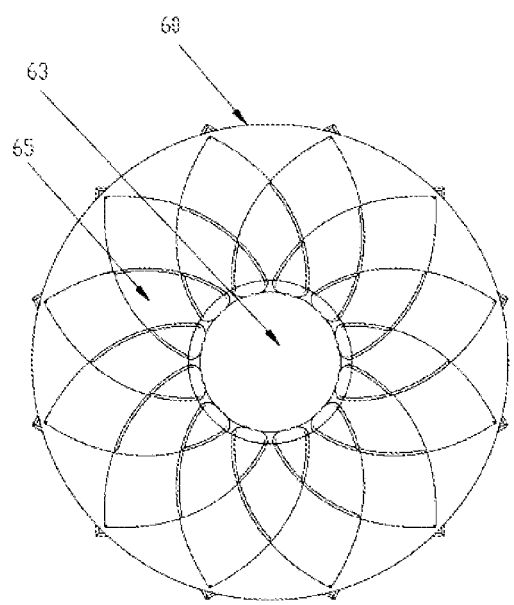
FIG. 33 is a side schematic structural diagram of an occluding stent in Embodiment 12 of the present invention.
Figure 34:
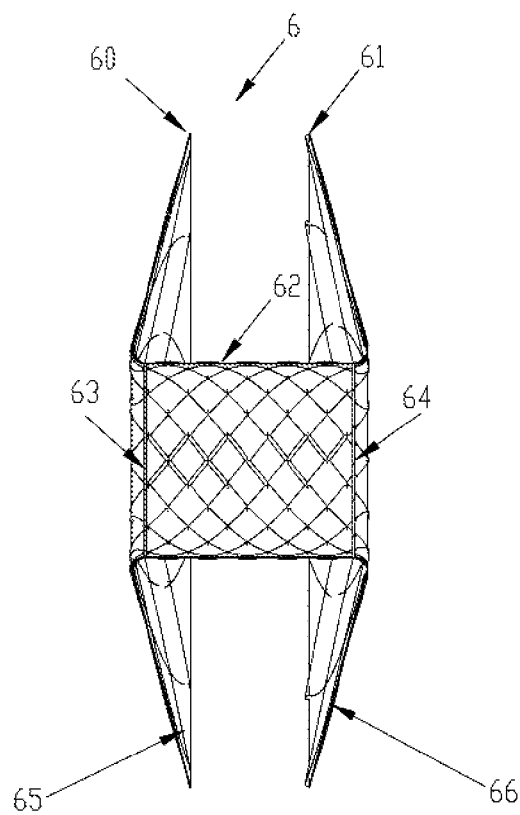
FIG. 34 is an overall schematic structural diagram of the occluding stent in Embodiment 12 of the present invention.
Figure 35:
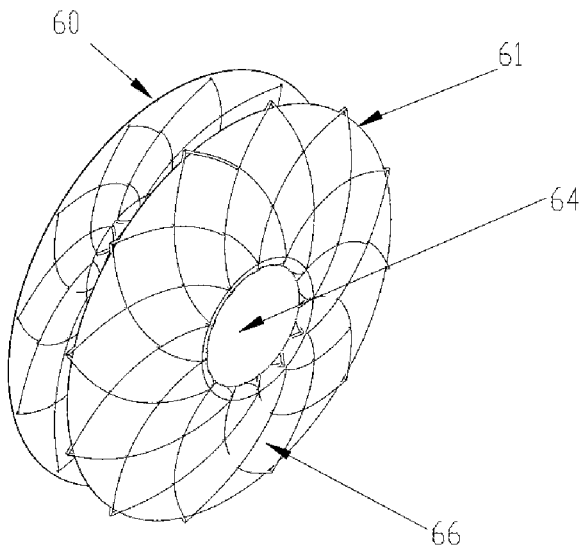
FIG. 35 is a first three-dimensional schematic diagram of the occluding stent in Embodiment 12 of the present invention.
Figure 36:
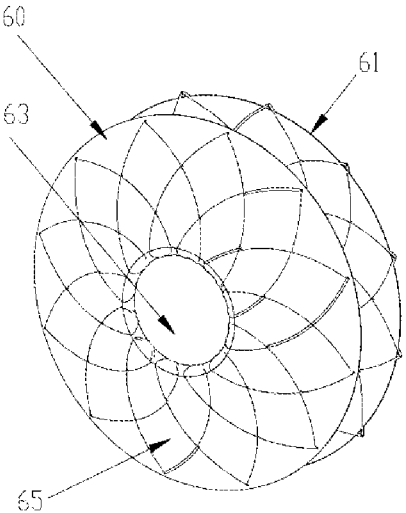
FIG. 36 is a second three-dimensional schematic diagram of the occluding stent in Embodiment 12 of the present invention.
Figure 37:
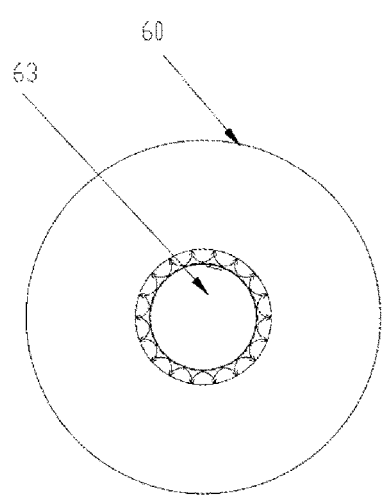
FIG. 37 is a side schematic structural diagram of an occluding stent in Embodiment 13 of the present invention.
Figure 38:
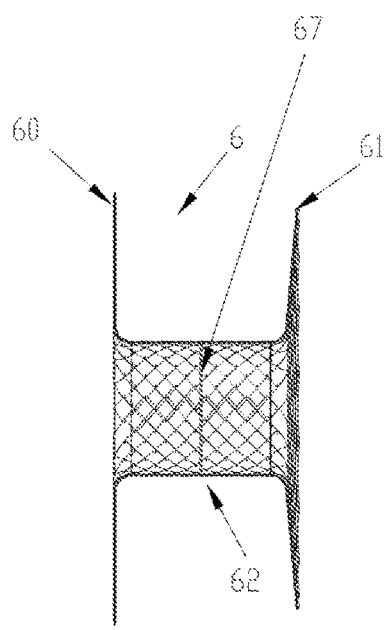
FIG. 38 is an overall schematic structural diagram of the occluding stent in Embodiment 13 of the present invention.
Figure 39:
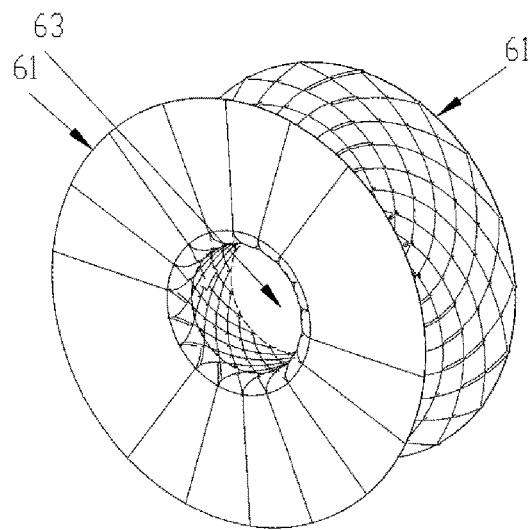
FIG. 39 is a first three-dimensional schematic diagram of the occluding stent in Embodiment 13 of the present invention.
Figure 40:
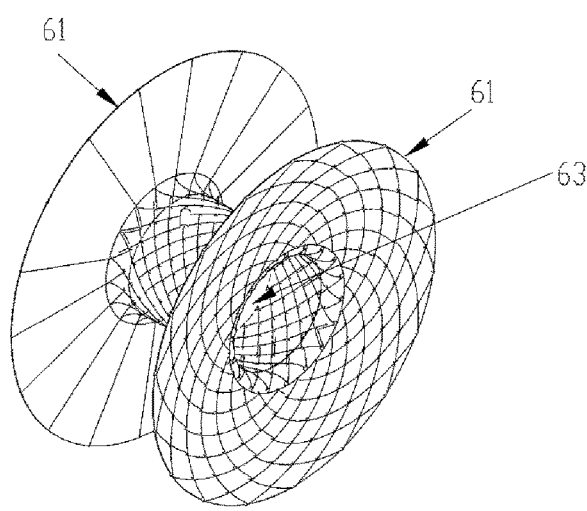
FIG. 40 is a second three-dimensional schematic diagram of the occluding stent in Embodiment 13 of the present invention.
Figure 41:
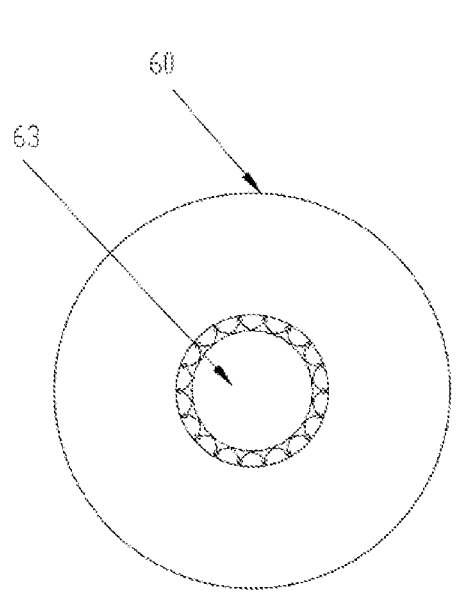
FIG. 41 is a side schematic structural diagram of an occluding stent in Embodiment 14 of the present invention.
Figure 42:
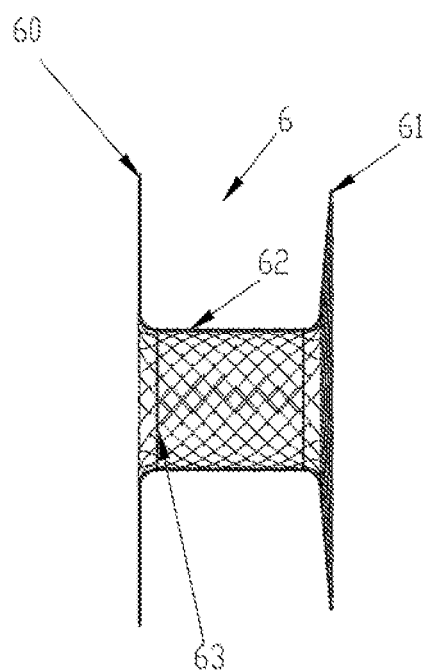
FIG. 42 is an overall schematic structural diagram of the occluding stent in Embodiment 14 of the present invention.
Figure 43:
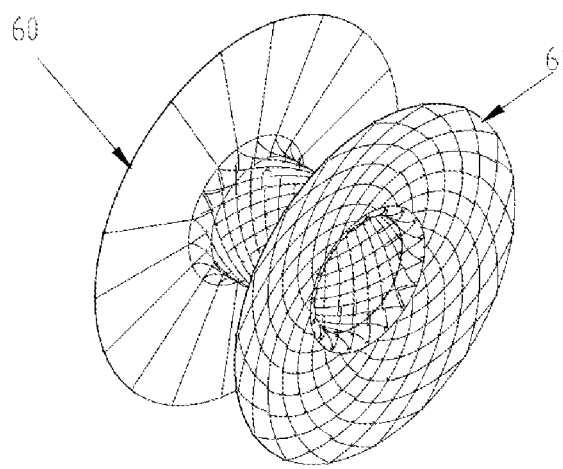
FIG. 43 is a first three-dimensional schematic diagram of the occluding stent in Embodiment 14 of the present invention.
Figure 44:
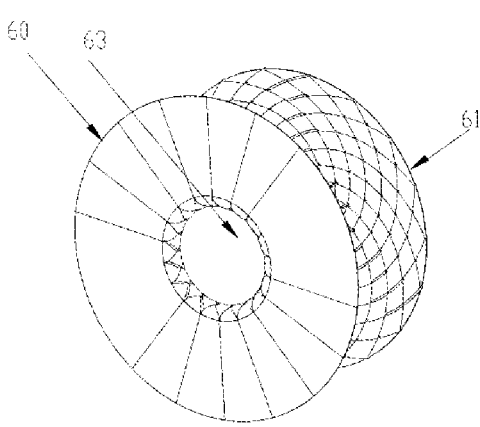
FIG. 44 is a second three-dimensional schematic diagram of the occluding stent in Embodiment 14 of the present invention.
Figure 45:
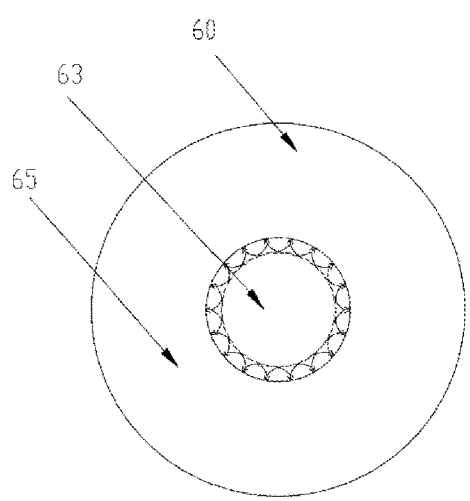
FIG. 45 is a side schematic structural diagram of an occluding stent in Embodiment 15 of the present invention.
Figure 46:
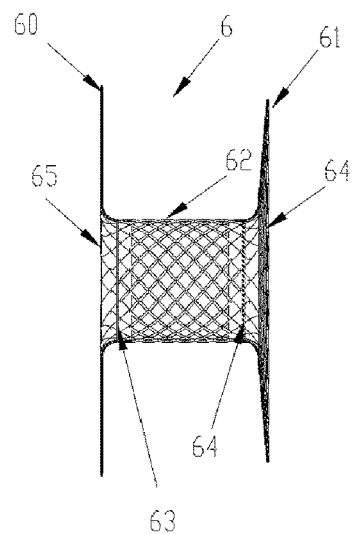
FIG. 46 is an overall schematic structural diagram of the occluding stent in Embodiment 15 of the present invention.
Figure 47:
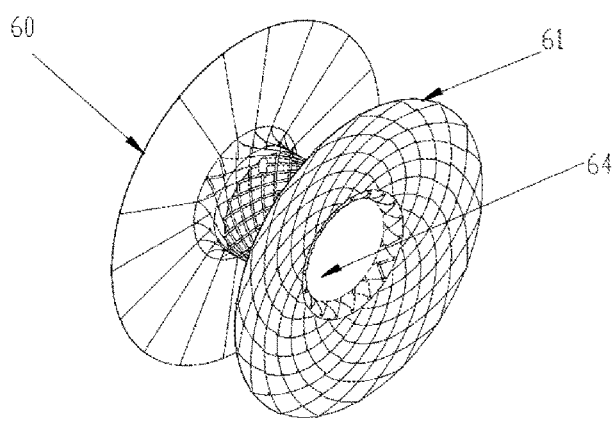
FIG. 47 is a first three-dimensional schematic diagram of the occluding stent in Embodiment 15 of the present invention.
Figure 48:
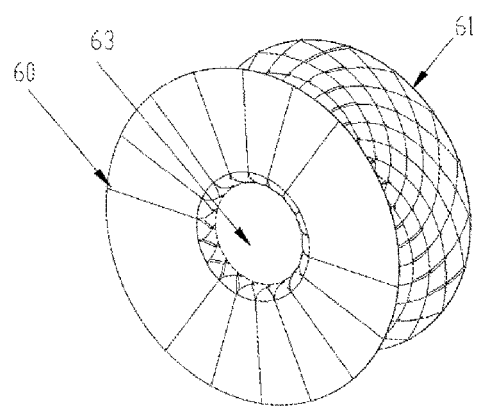
FIG. 48 is a second three-dimensional schematic diagram of the occluding stent in Embodiment 15 of the present invention.
Figure 49:
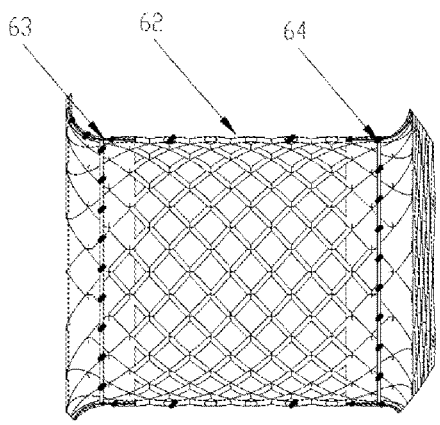
FIG. 49 is a partial schematic diagram of a connection portion of the occluding stent in Embodiment 15 of the present invention.

As shown in FIG. 21, the distal end of the front pusher 93 is rounded, to better push out the stent without damaging the occluding coating; the proximal end of the front pusher 93 is teardrop-shaped, so that it is more beautiful and easier to clean. The front pushrod 92 is further provided with a precise locating sleeve 95 at the proximal end, to limit relative positions of the front pushrod 92 and the inner connection hose 91, so that the stent can be precisely mounted at a specific position of the implanter.

Embodiment 8

As shown in FIG. 22 to FIG. 25,
an occluding stent 6 includes a distal flange occluding body 60, a proximal flange occluding body 61 and a connection portion 62; external surfaces of the distal flange occluding body 60, the proximal flange occluding body 61 and the connection portion 62 are all provided with a coating.

In addition, a first occluding coating 63 is provided between a first occluding portion end 65 on an external side of the distal flange occluding body 60 and an inner cavity of the connection portion 62; a second occluding coating 64 is provided between a second occluding end 66 on an external side of the proximal flange occluding body 61 and the inner cavity of the connection portion 62.

The distal flange occluding body 60 shapes like a bowl that is concave inward.

The first occluding coating 63 is provided between a diameter shrinkage area of the first occluding portion end 65 and the inner cavity of the connection portion 62.

The proximal flange occluding body 61 is umbrella-shaped or flare-shaped.

The second occluding coating 64 is provided between a diameter shrinkage area of the second occluding end 66 and the inner cavity of the connection portion 62.

Food or foreign objects are prevented from entering the trachea from the esophagus.

The coatings in this embodiment may be silicone coatings meeting medical standards or may be materials having a similar function.

Embodiment 9

As shown in FIG. 26 to FIG. 28,
an occluding stent 6 includes a distal flange occluding body 60, a proximal flange occluding body 61 and a connection portion 62; external surfaces of the distal flange occluding body 60, the proximal flange occluding body 61 and the connection portion 62 are all provided with a coating.

In addition, a first occluding coating 63 is provided between a first occluding portion end 65 on an external side of the distal flange occluding body 60 and an inner cavity of the connection portion 62; a second occluding coating 64 is provided between a second occluding end 66 on an external side of the proximal flange occluding body 61 and the inner cavity of the connection portion 62.

The distal flange occluding body 60 shapes like a bowl that is concave inward.

The first occluding coating 63 is provided between a diameter shrinkage area of the first occluding portion end 65 and the inner cavity of the connection portion 62.

The proximal flange occluding body 61 shapes like a bowl that is concave inward.

The second occluding coating 64 is provided between a diameter shrinkage area of the second occluding end 66 and the inner cavity of the connection portion 62.

Food or foreign objects are prevented from entering the trachea from the esophagus.

In addition, in this embodiment, a plurality of tantalum markers, for example, 4 tantalum markers, may be uniformly distributed on a single side of the stent.

The coatings in this embodiment may be silicone coatings meeting medical standards or may be materials having a similar function.

Embodiment 10

As shown in FIG. 29 to FIG. 32,
an occluding stent 6 includes a distal flange occluding body 60, a proximal flange occluding body 61 and a connection portion 62; external surfaces of the distal flange occluding body 60, the proximal flange occluding body 61 and the connection portion 62 are all provided with a coating.

In addition, a first occluding coating 63 is provided between a first occluding portion end 65 on an external side of the distal flange occluding body 60 and an inner cavity of the connection portion 62; a second occluding coating 64 is provided between a second occluding end 66 on an external side of the proximal flange occluding body 61 and the inner cavity of the connection portion 62.

The distal flange occluding body 60 is disc-shaped or umbrella-shaped.

The first occluding coating 63 is provided between a diameter shrinkage area of the first occluding portion end 65 and the inner cavity of the connection portion 62.

The proximal flange occluding body 61 is disc-shaped or umbrella-shaped.

The second occluding coating 64 is provided between a diameter shrinkage area of the second occluding end 66 and the inner cavity of the connection portion 62.

Food or foreign objects are prevented from entering the trachea from the esophagus.

The coatings in this embodiment may be silicone coatings meeting medical standards or may be materials having a similar function.

Embodiment 11

As shown in FIG. 33 to FIG. 36, an occluding stent 6 includes a distal flange occluding body 60, a proximal flange occluding body 61 and a connection portion 62; external surfaces of the distal flange occluding body 60, the proximal flange occluding body 61 and the connection portion 62 are all provided with a coating.

In addition, a first occluding coating 63 is provided between a first occluding portion end 65 on an external side of the distal flange occluding body 60 and an inner cavity of the connection portion 62; a second occluding coating 64 is provided between a second occluding end 66 on an external side of the proximal flange occluding body 61 and the inner cavity of the connection portion 62.

The distal flange occluding body 60 is umbrella-shaped, and provides coverage towards an internal side. That is, if the first occluding portion end 65 is compared to an umbrella surface, the umbrella surface faces outwards.

The first occluding coating 63 is provided between the first occluding portion end 65 and the inner cavity of the connection portion 62.

The proximal flange occluding body 61 is umbrella-shaped, and provides coverage towards an internal side. That is, if the first occluding portion end 65 is compared to an umbrella surface, the umbrella surface faces outwards.

The second occluding coating 64 is provided between the second occluding end 66 and the inner cavity of the connection portion 62.

Food or foreign objects are prevented from entering the trachea from the esophagus.

The coatings in this embodiment may be silicone coatings meeting medical standards or may be materials having a similar function.

Embodiment 12

As shown in FIG. 37 to FIG. 40, an occluding stent 6 includes a distal flange occluding body 60, a proximal flange occluding body 61 and a connection portion 62; external surfaces of the distal flange occluding body 60, the proximal flange occluding body 61 and the connection portion 62 are all provided with a coating.

The distal flange occluding body 60 is umbrella-shaped or disc-shaped.

An inner cavity of the connection portion 62 is provided with a third occluding coating 67.

The proximal flange occluding body 61 is umbrella-shaped or disc-shaped.

The middle of a cavity channel of the connection portion 62 is plugged with silicone. Neither end of the connection portion 62 is plugged, or one of the two ends of the connection portion 62 is plugged. Food or foreign objects are prevented from entering the trachea from the esophagus.

The coatings in this embodiment may be silicone coatings meeting medical standards or may be materials having a similar function.

Embodiment 13

As shown in FIG. 41 to FIG. 44, an occluding stent 6 includes a distal flange occluding body 60, a proximal flange occluding body 61 and a connection portion 62; external surfaces of the distal flange occluding body 60, the proximal flange occluding body 61 and the connection portion 62 are all provided with a coating.

The distal flange occluding body 60 is disc-shaped or umbrella-shaped.

The proximal flange occluding body 61 is disc-shaped or umbrella-shaped.

A first occluding coating 63 is provided between a diameter shrinkage area of a first occluding portion end 65 and an inner cavity of the connection portion 62, or a second occluding coating 64 is provided between a diameter shrinkage area of a second occluding end 66 and the inner cavity of the connection portion 62. That is, the cavity channel at only one end of the connection portion 62 is plugged with silicone, while the other end is not plugged.

The proximal flange occluding body 61 is disc-shaped or umbrella-shaped. In the figures, the first occluding coating 63 being provided between the diameter shrinkage area of the first occluding portion end 65 and the inner cavity of the connection portion 62 is used as an example.

Food or foreign objects are prevented from entering the trachea from the esophagus.

The coatings in this embodiment may be silicone coatings meeting medical standards or may be materials having a similar function.

Embodiment 14

As shown in FIG. 45 to FIG. 49, an occluding stent 6 includes a distal flange occluding body 60, a proximal flange occluding body 61 and a connection portion 62; external surfaces of the distal flange occluding body 60 and the proximal flange occluding body 61 are both provided with a coating. An external surface of the connection portion 62 is partially provided with a coating. Specifically, a middle part of the external surface of the connection portion 62 is directly exposed, and both ends of the external surface are provided with the coating.

The distal flange occluding body 60 is disc-shaped or umbrella-shaped.

The proximal flange occluding body 61 is disc-shaped or umbrella-shaped.

A first occluding coating 63 is provided between a diameter shrinkage area of a first occluding portion end 65 and an inner cavity of the connection portion 62, and/or a second occluding coating 64 is provided between a diameter shrinkage area of a second occluding end 66 and the inner cavity of the connection portion 62.

Food or foreign objects are prevented from entering the trachea from the esophagus.

The coatings in this embodiment may be silicone coatings meeting medical standards or may be materials having a similar function.

In the foregoing embodiments, the placement position of the distal flange occluding body 60 is not limited to the esophageal side or the trachea side; the placement position of the proximal flange occluding body 61 is not limited to the esophageal side or the trachea side; the connection portion 62 is placed between the esophagus and the trachea, but it is not excluded that a small part of or more than half of the connection portion 62 is located on the esophageal side or the trachea side.

Embodiment 15

Figure 50:
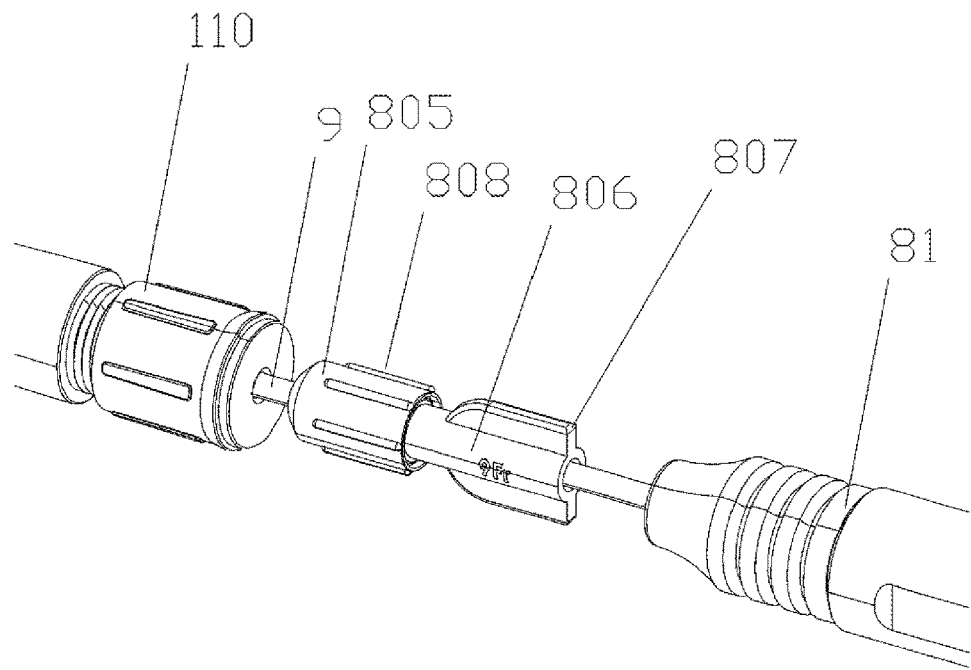
FIG. 50 is a schematic structural diagram of a range-adjustable mark in Embodiment 16 of the present invention.

FIG. 50 is a schematic structural diagram of a range-adjustable mark in Embodiment 16 of the present invention.

A range-adjustable mark is provided on a rear pushrod 9 between a rear pushrod locking knob 110 and a rear-handle front cover 81 of an implanter. The range-adjustable mark includes a positioning nut 805 at a distal end and a range adjuster 806 that is located at a proximal end and connected to the positioning nut 805 through threads. The positioning nut 805 is provided with an anti-slip rib 808, and the range adjuster 806 is provided with an alary protrusion 807. The positioning nut 805 and the range adjuster 806 are sleeved over the rear pushrod 9. The range adjuster 806 is screwed in or out, to adjust a distance between the rear pushrod locking knob 110 and the rear-handle front cover 81.

The range-adjustable mark is used for instructing the distal occluding portion body of the occluding stent to open. In the process of pushing the rear handle to the distal end, when the distance between the rear pushrod locking knob 110 and the rear-handle front cover 81 is completely occupied by the range-adjustable mark, it indicates that the rear handle is pushed to a predetermined position, that is, the distal occluding portion body of the occluding stent has been opened. Then, the rear handle is not pushed any more, and the implanter is pulled out towards the proximal end, so that the proximal occluding portion body of the occluding stent is open, to complete stent implanting and occlusion between the esophagus and the trachea.

The range-adjustable mark is applicable to an implanter through which a guide wire is passed or no guide wire is passed.

Embodiment 16

Figure 51:
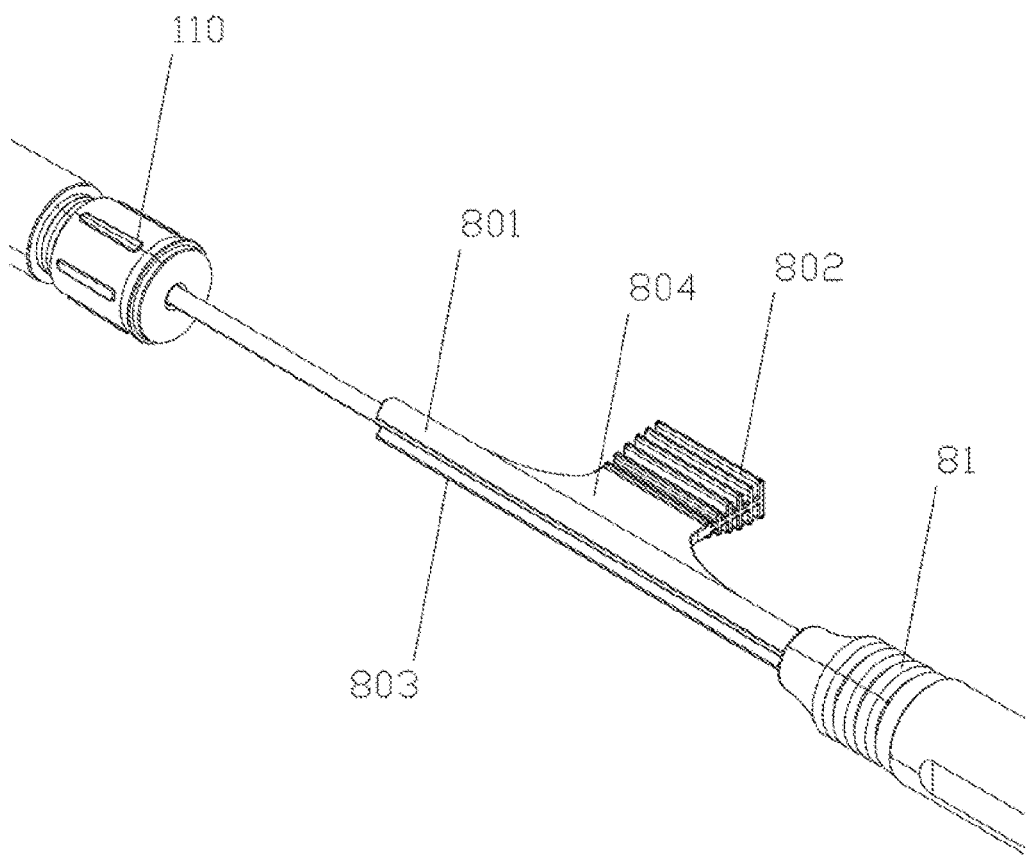
FIG. 51 is a schematic structural diagram of a removable mark in Embodiment 17 of the present invention.

FIG. 51 is a schematic structural diagram of a removable mark in Embodiment 17 of the present invention.

A removable mark is provided on a rear pushrod 9 between a rear pushrod locking knob 110 and a rear-handle front cover 81 of an implanter. The removable mark is sleeved over the rear pushrod 9 and includes a removable sleeve 801 and an anti-slip handle 802. The removable sleeve 801 and the anti-slip handle 802 are connected through a connector 804. A notch 803 for allowing the rear pushrod 9 to enter is provided on a side of the removable sleeve 801. The removable mark may be sleeved over the rear pushrod 9 through the notch 803. The connection is implemented relying on an elastic force of the removable sleeve 801, so that the distance between the rear pushrod locking knob 110 and the rear-handle front cover 81 is locked.

The removable mark is used for instructing the distal occluding portion body of the occluding stent to open. In the process of pushing the rear handle to the distal end, when the distance between the rear pushrod locking knob 110 and the rear-handle front cover 81 is completely occupied by the removable mark, it indicates that the rear handle is pushed to a predetermined position, that is, the distal occluding portion body of the occluding stent has been opened. Then, the rear handle is not pushed any more, and the implanter is pulled out towards the proximal end, so that the proximal occluding portion body of the occluding stent is open, to complete stent implanting and occlusion between the esophagus and the trachea.

The removable mark is applicable to an implanter through which a guide wire is passed or no guide wire is passed.

Embodiment 17

The occluding stent implanter is further provided with an inner hole to allow a guide wire to pass through from a side of the occluding stent.

Basic principles, main features and advantages of the present invention are shown and described above. A person skilled in the art should understand that the present invention is not limited to the foregoing embodiments. The foregoing embodiments and the embodiments described in the specification are merely exemplary embodiments of the present invention, which are not intended to limit the present invention. The present invention may have various changes and improvements without departing from the spirit and scope of the present invention, and all these changes and improvements fall within the protection scope of the present invention. The protection scope of the present invention are subject to the appended claims and equivalents thereof.

What is claimed is:

1. An occluding stent, comprising a distal flange occluding body, a proximal flange occluding body, and a connection portion, wherein surfaces of both a distal most end of the distal flange occluding body and a proximal most end of the proximal flange occluding body are away from the connection portion in a longitudinal direction of the connection portion and are flat, and metal wires of the distal most end and the proximal most end are continually braided, wherein the distal flange occluding body is umbrella-shaped, mushroom cap-shaped, disc-shaped, hemispherical, or spherical, and the proximal flange occluding body is umbrella-shaped, flare-shaped, mushroom cap-shaped, or spherical a sealed occlusion state is formed between the distal flange occluding body and the proximal flange occluding body by using a coating, and the coating simultaneously comprises at least one and the coating comprises a first occluding coating provided only between the distal flange occluding body and an inner cavity of the connection portion, a second occluding coating provided only between the proximal flange occluding body and the inner cavity of the connection portion, and a third occluding coating provided only in the inner cavity of the connection portion in a vertical direction of the connection portion to prevent food or foreign objects from passing through the inner cavity of the connection portion.

2. The occluding stent according to claim 1, wherein a surface of the connection portion is wholly or partially provided with a fourth coating; a surface of the distal flange occluding body is wholly or partially provided with a fifth coating; and a surface of the proximal flange occluding body is wholly or partially provided with a sixth coating.

3. An implanter for the occluding stent according to claim 1, wherein the occluding stent is loaded at a distal end of an outer tube, a proximal end of the outer tube is connected to a front handle, a middle tube is located in the outer tube, and the middle tube is connected to a rear handle; the front handle is retracted, the outer tube retreats, and the middle tube ejects and releases the distal flange occluding body of the occluding stent; the implanter is retracted into a proximal tissue, and then the proximal flange occluding body of the occluding stent is deployed.

4. An implanter for the occluding stent according to claim 1, comprising a rear handle, a rear pushrod, and a front handle, wherein the rear pushrod is fixedly connected to the rear handle, the rear pushrod passes through an interior of the front handle, a distal end of the rear pushrod is connected to a front pushrod through an inner connection hose, a mushroom-shaped front pusher is connected at a distal end of the front pushrod, a flexible tube is sleeved outside the front pushrod, a proximal end of the front handle is connected to a rear pushrod locking knob through threads, a distal end of the rear pushrod locking knob is provided with a tapered rubber plug, and the tapered rubber plug is in contact with a tapered inner wall inside the front handle.

5. The implanter for the occluding stent according to claim 4, wherein a proximal end of the rear handle is provided with a rear-handle rear cover, a rear-handle front cover is connected at a distal end of the rear handle, and the rear pushrod is fixedly connected to the rear handle through a rear pushrod holder; the front handle is provided with a Luer taper tube in communication with an inner cavity of the front handle, a distal end of the front handle is connected to a front-handle front cover through a connecting sleeve, and a distal end of the front-handle front cover is provided with a flexible sleeve hose connecting tube; a flexible tube is connected on the sleeve hose connecting tube; the tapered rubber plug is provided with a through hole for the rear pushrod to pass through, the tapered rubber plug has a tapered surface in contact with the tapered inner wall, and the tapered rubber plug is provided with a cross recess.

6. The implanter for the occluding stent according to claim 4, wherein a range-adjustable mark is provided on the rear pushrod between the rear pushrod locking knob and a rear-handle front cover of the implanter, the range-adjustable mark comprises a positioning nut located at a distal end and a range adjuster that is located at a proximal end and connected to the positioning nut through threads, the positioning nut is provided with an anti-slip rib, the range adjuster is provided with an alary protrusion, the positioning nut and the range adjuster are sleeved over the rear pushrod, and the range adjuster is screwed in or out to adjust a distance between the rear pushrod locking knob and the rear-handle front cover.

7. The implanter for the occluding stent according to claim 4, wherein a removable mark is provided on the rear pushrod between the rear pushrod locking knob and a rear-handle front cover of the implanter, the removable mark is sleeved over the rear pushrod and comprises a removable sleeve and an anti-slip handle, the removable sleeve and the anti-slip handle are connected through a connector, a notch for allowing the rear pushrod to enter is provided on a side of the removable sleeve, the removable mark is sleeved over the rear pushrod through the notch, and a connection is implemented relying on an elastic force of the removable sleeve, so that a distance between the rear pushrod locking knob and the rear-handle front cover is locked.

8. The occluding stent according to claim 1, wherein the first occluding coating and the second occluding coating are provided to prevent food or foreign objects from entering from one alimentary canal into another alimentary canal, from one airway into one alimentary canal, from one alimentary canal into one airway or from one airway into another airway.

9. The occluding stent according to claim 1, wherein the first occluding coating or the second occluding coating or the third occluding coating is provided to prevent food or foreign objects from entering from one alimentary canal into another alimentary canal, from one airway into one alimentary canal, from one alimentary canal into one airway or from one airway into another airway.

10. The occluding stent according to claim 1, wherein the first occluding coating, the second occluding coating, and the third occluding coating are provided to prevent food or foreign objects from entering from one alimentary canal into another alimentary canal, from one airway into one alimentary canal, from one alimentary canal into one airway or from one airway into another airway.

* * * * *